United States Patent
Al-Ali et al.

(10) Patent No.: US 7,373,193 B2
(45) Date of Patent: May 13, 2008

(54) PULSE OXIMETRY DATA CAPTURE SYSTEM

(75) Inventors: Ammar Al-Ali, Tustin, CA (US); Bilal Muhsin, Aliso Viejo, CA (US); Michael Lee, Aliso Viejo, CA (US)

(73) Assignee: Masimo Corporation, Irvine, CA (US)

( * ) Notice: Subject to any disclaimer, the term of this patent is extended or adjusted under 35 U.S.C. 154(b) by 198 days.

(21) Appl. No.: 10/983,048

(22) Filed: Nov. 5, 2004

(65) Prior Publication Data

US 2005/0101849 A1 May 12, 2005

Related U.S. Application Data

(60) Provisional application No. 60/518,051, filed on Nov. 7, 2003.

(51) Int. Cl.
*A61B 5/1455* (2006.01)
(52) U.S. Cl. .................. 600/323; 600/310; 600/324
(58) Field of Classification Search ............... 600/300, 600/323, 324, 322
See application file for complete search history.

(56) References Cited

U.S. PATENT DOCUMENTS

| | | |
|---|---|---|
| 4,960,128 A | 10/1990 | Gordon et al. |
| 5,163,438 A | 11/1992 | Gordon et al. |
| 5,337,744 A | 8/1994 | Branigan |
| 5,431,170 A | 7/1995 | Mathews |
| 5,452,717 A | 9/1995 | Branigan et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,590,649 A | 1/1997 | Caro et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| 5,701,894 A * | 12/1997 | Cherry et al. ............... 600/300 |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |

(Continued)

*Primary Examiner*—Eric Winakur
*Assistant Examiner*—Etsub D Berhanu
(74) *Attorney, Agent, or Firm*—Knobbe, Martens, Olson & Bear, LLP (57) ABSTRACT

A data capture system utilizes a sensor with emitters adapted to transmit light into a fleshy medium and a detector adapted to generate intensity signals in response to receiving light after absorption by the fleshy medium. A monitor is configured to input the intensity signals, generate digitized signals from the intensity signals at a sampling rate and compute at least one physiological parameter responsive to magnitudes of the digitized signals. A data storage device is integrated with the monitor and is adapted to record data derived from the digitized signals on a removable storage media at the sampling rate.

21 Claims, 8 Drawing Sheets

U.S. PATENT DOCUMENTS

| | | |
|---|---|---|
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,622 A * | 9/2000 | Minoz .................. 600/361 |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,334,065 B1 | 12/2001 | Al-Ali et al. |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,397,092 B1 * | 5/2002 | Norris et al. ............... 600/323 |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,515,273 B2 | 2/2003 | Al-Ali |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,725,075 B2 | 4/2004 | Al-Ali |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 2002/0161291 A1 * | 10/2002 | Kianl et al. ............... 600/324 |

* cited by examiner

FIG. 5E (SECTION A-A)

PULSE OXIMETRY DATA CAPTURE SYSTEM

CROSS-REFERENCE TO RELATED APPLICATIONS

This application relates to and claims the benefit of prior U.S. Provisional Patent Application No. 60/518,051 entitled Pulse Oximetry Trend Data Storage System, filed Nov. 7, 2003 and incorporated by reference herein.

BACKGROUND OF THE INVENTION

Figure 1:
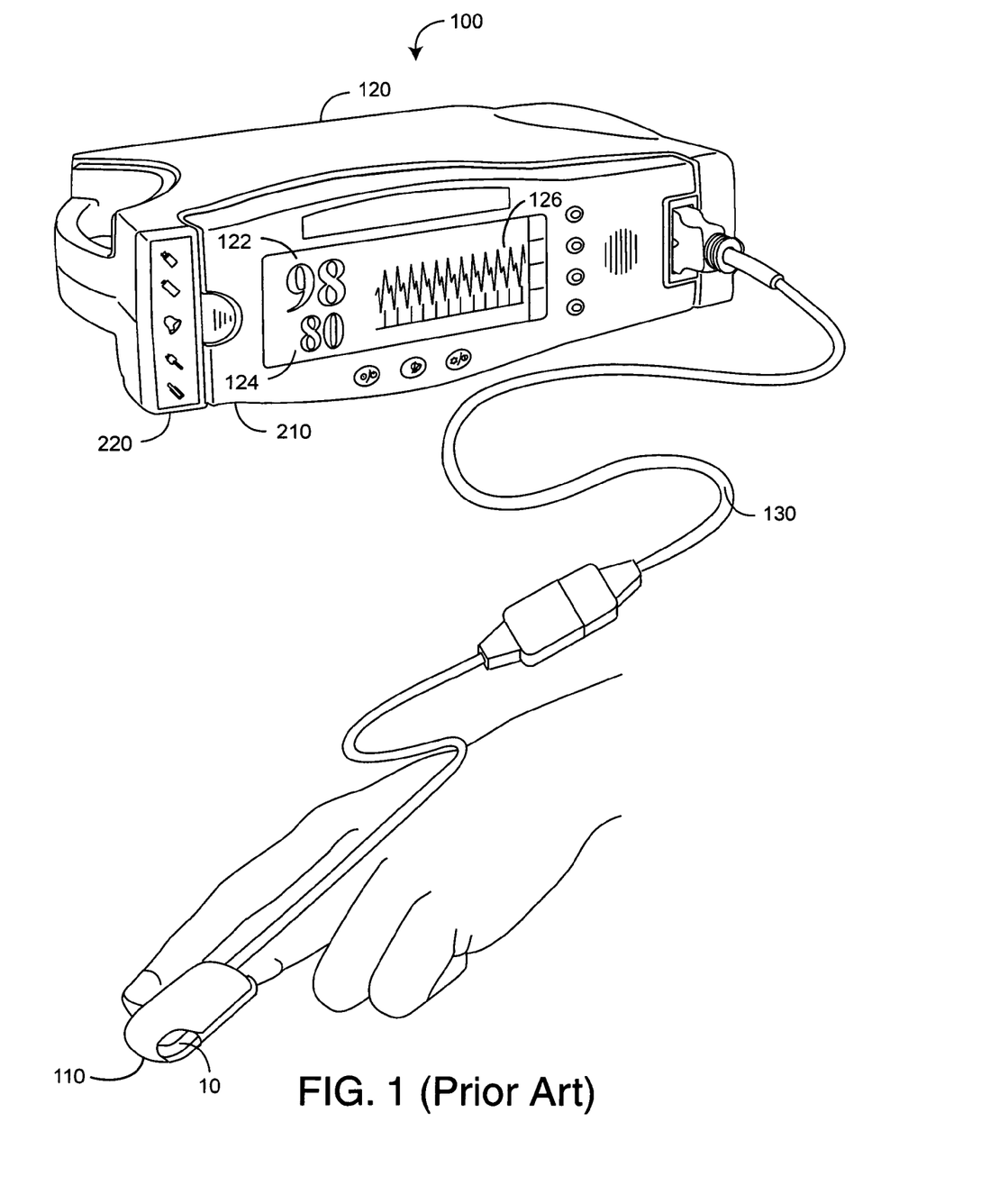
FIG. 1 is a perspective view of a prior art pulse oximetry system having a portable pulse oximeter and a docking station.

Pulse oximeters have gained rapid acceptance in a wide variety of medical applications, including surgical wards, intensive care units, general wards and home care by providing early detection of decreases in the arterial oxygen supply, reducing the risk of accidental death and injury. FIG. 1 illustrates a pulse oximetry system 100 having a sensor 110 applied to a patient, a monitor 120, and a patient cable 130 connecting the sensor 110 and the monitor 120. The sensor 110 has emitters (not shown) and a detector (not shown) and is attached to a patient at a selected fleshy medium site, such as a fingertip 10 as shown or an ear lobe. The emitters are positioned to project light of at least two wavelengths through the blood vessels and capillaries of the fleshy medium. The detector is positioned so as to detect the emitted light after absorption by the fleshy medium, including hemoglobin and other constituents of pulsatile blood flowing within the fleshy medium, generating at least first and second intensity signals in response. A pulse oximetry sensor is described in U.S. Pat. No. 6,256,523 entitled Low Noise Optical Probes, and a pulse oximetry monitor is described in U.S. Pat. No. 6,745,060 entitled Signal Processing Apparatus, both assigned to Masimo Corporation, Irvine, Calif. and both incorporated by reference herein.

The monitor 120, which may be a standalone device or may be incorporated as a module or built-in portion of a multiparameter patient monitoring system, computes at least one physiological parameter responsive to magnitudes of the intensity signals. A monitor 120 typically provides a numerical readout of the patient's oxygen saturation 122, a numerical readout of pulse rate 124, and a display of the patient's plethysmograph 126, which provides a visual display of the patient's pulse contour and pulse rate.

In one embodiment, the pulse oximetry system 100 has a portable instrument 210 and a docking station 220, such as described in U.S. Pat. No. 6,584,336 entitled Universal/Upgrading Pulse Oximeter, assigned to Masimo Corporation, Irvine, Calif. and incorporated by reference herein. The portable 210 is a battery operated, fully functional, standalone pulse oximeter monitor, as described above, which can be installed into the docking station 220 to expand its functionality.

Figure 2:
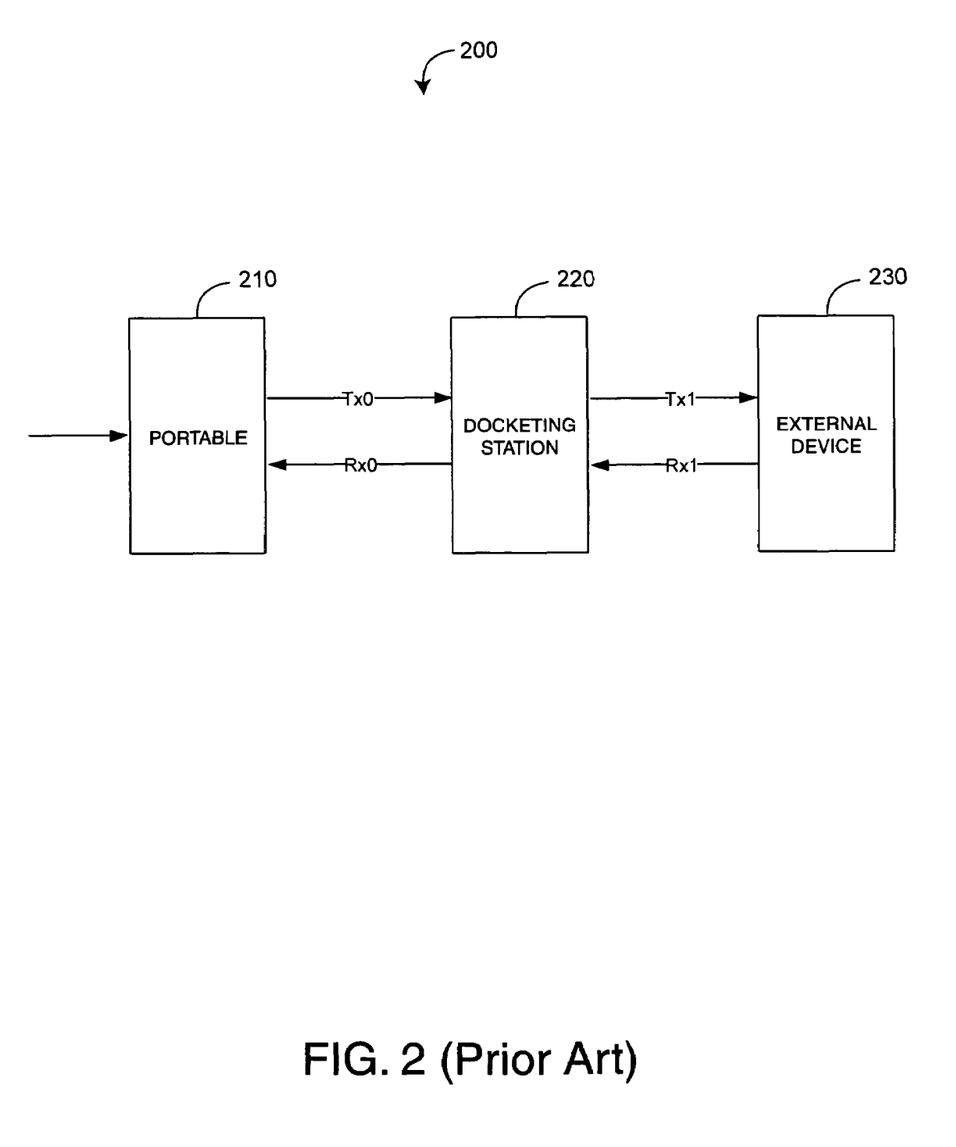
FIG. 2 is a block diagram of portable and docking station data communications.

FIG. 2 illustrates data communications for the portable 210 and docking station 220. The portable 210 has bi-directional serial data communications with the docking station 220 using universal asynchronous receive, Rx0, and transmit, Tx0, (UART) signals, and the docking station 220 has bi-directional serial data communications with an external device 230 using Tx1 and Rx1 UART signals.

SUMMARY OF THE INVENTION

A conventional pulse oximeter may store trend data that consists of, for example, oxygen saturation and pulse rate. This data is recorded at a low rate, such as 1 Hz. Although the resolution afforded by a low data rate is fine for many patient diagnostic purposes, it is desirable to store the plethysmograph waveform, other pulse oximeter parameters and various internal data at a high rate, such as the sensor signal sampling rate. The resulting high resolution data advantageously assists and/or improves patient condition evaluation, pulse oximetry exception diagnosis and algorithm development. Further, pulse oximetry data is conventionally stored using an external computer or a laptop, which may not always be available or is otherwise cumbersome.

A pulse oximetry data capture system advantageously replaces an external computer with a small data storage device that utilizes removable storage media to hold many hours of high resolution data. In one embodiment, the data storage device is integrated into a docking station for a portable instrument. The removable storage media, having been written with data, can be easily shipped off-site from where the data is collected for later analysis.

One aspect of a pulse oximetry data capture system is a sensor having emitters adapted to transmit light of at least first and second wavelengths into a fleshy medium. A detector is adapted to generate at least first and second intensity signals in response to receiving light after absorption by constituents of pulsatile blood flowing within the fleshy medium. A monitor is configured to input the intensity signals, generate digitized signals from the intensity signals at a sampling rate and compute at least one physiological parameter responsive to magnitudes of the digitized signals. A data storage device is integrated with the monitor and is adapted to record data derived from the digitized signals on a removable storage media at the sampling rate.

Another aspect of a pulse oximetry data capture system is a method having the steps of emitting light of at least first and second wavelengths and detecting the light after absorption by a fleshy tissue site so as to generate a corresponding sensor signal. Additional steps are digitizing at a sampling rate, demodulating the sensor signal so as to generate a plethysmograph, and calculating at least oxygen saturation and pulse rate from the plethysmograph. A further step is writing data to the removable media. The data comprises the plethysmograph at the sampling frequency along with the oxygen saturation and the pulse rate at a sub-sampling frequency.

A further aspect of a data capture system has a sensor adapted to generate an intensity signal responsive to light absorption by constituents of pulsatile blood flowing within a fleshy medium. A digitizer inputs the intensity signal and generates a digital plethysmograph signal at a sampling rate. A signal processor inputs the plethysmograph and calculates an oxygen saturation and pulse rate. A storage media is configured to removably load into a data storage device. The data storage device inputs the plethysmograph, oxygen saturation and pulse rate and writes the plethymograph to the storage media at the sampling rate, along with the oxygen saturation and the pulse rate at a sub-sampling rate.

DETAILED DESCRIPTION OF THE PREFERRED EMBODIMENTS

Figure 3:
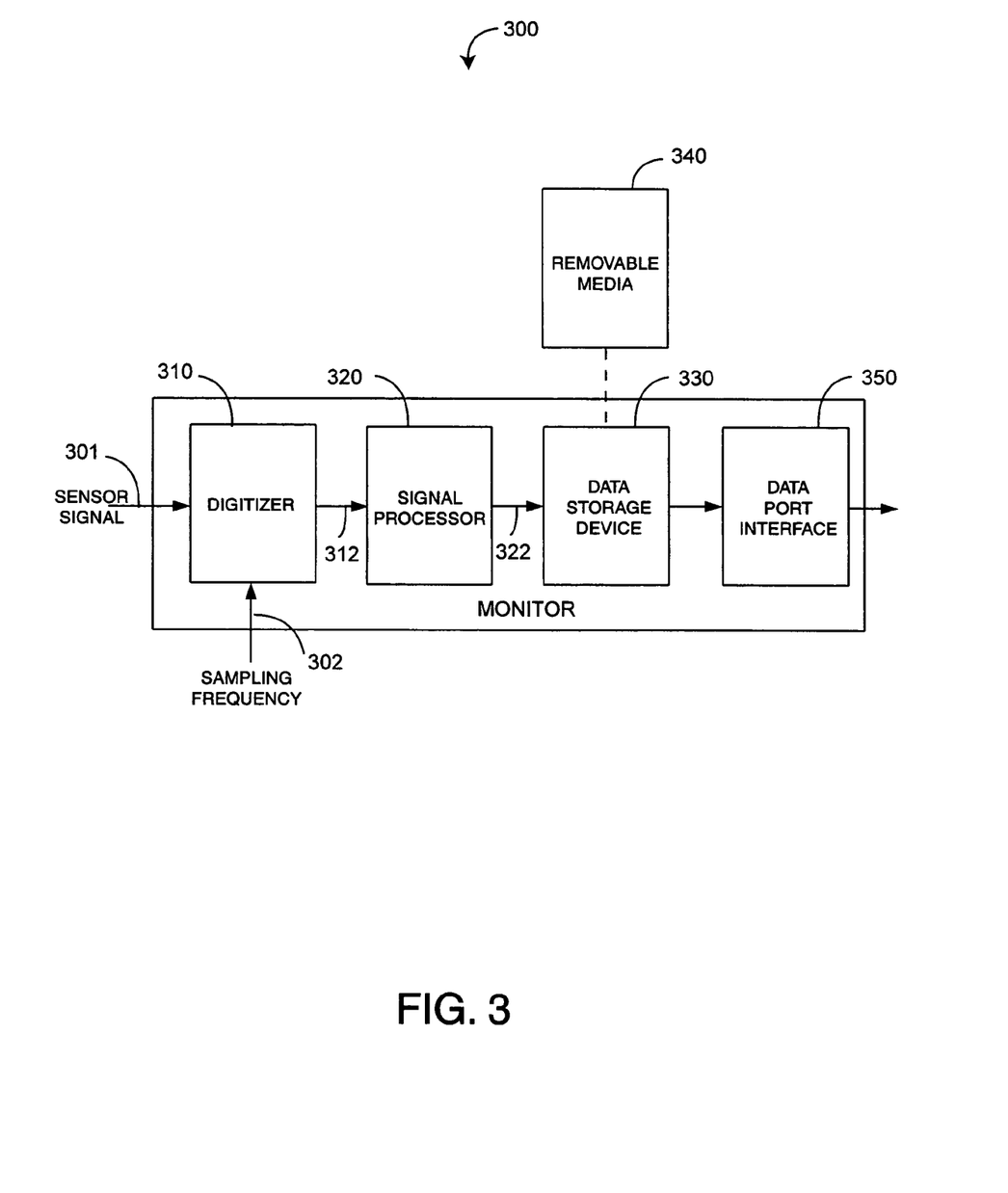
FIG. 3 is a general block diagram of a pulse oximetry data capture system.

FIG. 3 illustrates a pulse oximetry data capture system 300 having a digitizer 310, signal processor 320, a data storage device 330, a removable media 340 and a data port interface 350. The digitizer 310 samples the sensor signal 301 based upon a predetermined sampling frequency 302 and performs an analog-to-digital conversion of the sampled signal to generate a digitized sensor signal 312. The signal processor 320 demodulates the red (RD) and IR components of the digitized sensor signal 312 into RD and IR plethysmograph signals and operates on those plethysmograph signals so as to calculate oxygen saturation and pulse rate. A pulse oximetry demodulator is described in U.S. Pat. No. 6,643,530 entitled Method and Apparatus for Demodulating Signals in a Pulse Oximetry System, assigned to Masimo Corporation, Irvine, Calif. and incorporated by reference herein. As a result, the signal processor 320 generates a data stream 322 comprising plethysmograph, oxygen saturation and pulse rate values among other data. The data storage device 330 inputs the data stream 322, which is recorded on the removable media 340. The data stream 322 may also be provided to an external device via the data port interface 350. In various embodiments, the data storage device 330 may transparently "pass-through" the data stream 322 to other system components, such as the data port interface 350, or it may otherwise tap the data stream 322 as it is utilized elsewhere in the system 300. Alternatively, the signal processor 320 or other system components may provide the data storage device 330 with a dedicated data stream used solely for data recording purposes.

In one embodiment, the data stream 322 comprises raw, filtered and/or scaled plethysmograph waveform data; computed output data such as oxygen saturation, pulse rate, signal strength and signal quality; and other system data such as sensor status, monitor status, monitor settings, alarms, and internal algorithm parameters and variables. Pulse oximetry signal strength and signal quality or confidence data are described in U.S. Pat. No. 6,463,311 entitled Plethysmograph Pulse Recognition Processor and U.S. Pat. No. 6,684,090 entitled Pulse Oximetry Data Confidence Indicator, both assigned to Masimo Corporation, Irvine, Calif. and both incorporated by reference herein. Sensor status, monitor status and settings and alarms are described in U.S. Pat. No. 6,658,276 entitled Pulse Oximeter User Interface, also assigned to Masimo Corporation and incorporated by reference herein.

Figure 4:
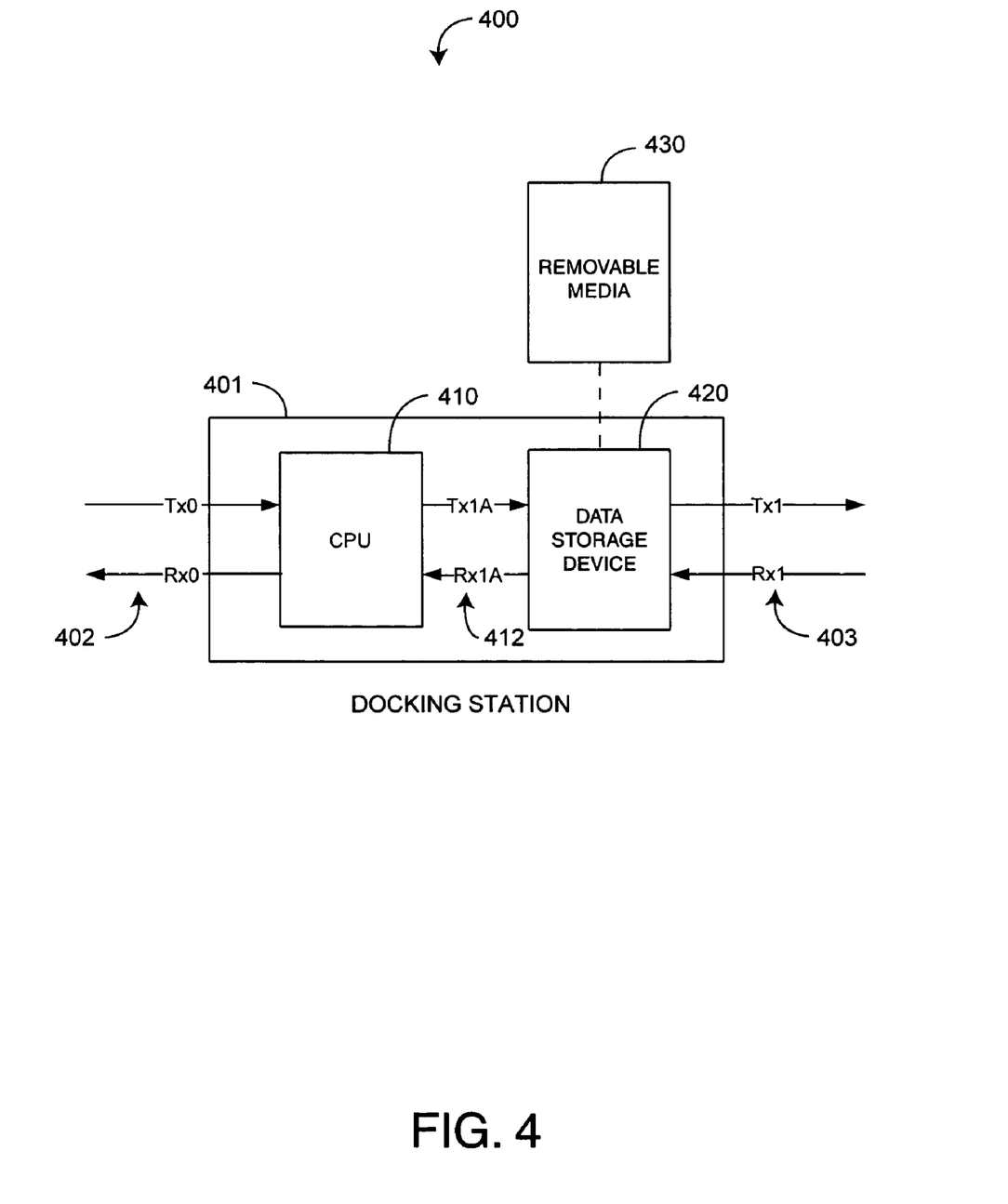
FIG. 4 is a block diagram of a pulse oximetry docking station incorporating a data capture system.

FIG. 4 illustrates a docking station embodiment 400 of a data capture system 300 (FIG. 3). A docking station 401 has a CPU 410, a data storage device 420 and an associated removable storage media 430. The docking station communicates with a portable pulse oximeter via input UART signals 402 and with an external device via output UART signals 403. The docking station CPU 410 communicates with the data storage device 420 using internal UART signals 412. The CPU 410 receives pulse oximetry and related data from the portable via the input UART signals 402 and may generate additional data in response. The received portable data and/or the CPU generated data is transmitted to the data storage device 420 via the internal UART signals 412 and recorded on the removable media 430 accordingly, as described in further detail below.

FIGS. 5A-E illustrate a particular docking station embodiment 500 of a pulse oximetry data capture system 400 (FIG. 4). The data storage device 520 (FIG. 5E) is a Flashcore-B available from TERN, Inc., Davis, Calif., and the removable storage media 530 (FIG. 5E) is a 256 MB Compact Flash card. The data storage device 520 is installed internally to the docking station 510 adjacent a circuit board 540 (FIG. 5E) and proximate the docking station bottom 501. The docking station 510 supplies power to the data storage device 520. The data storage device 520 transparently passes-through the internal UART signals 412 (FIG. 4) to the output UART signals 403 (FIG. 4). A slot 550 is created in the bottom of the docking station 510, which allows insertion and removal of the storage media 530 into and out of the storage device 520. One of ordinary skill will recognize that the data storage device 520 and associated removable media 530 can utilize various data storage technologies other than Compact Flash, such as Memory Stick, SmartMedia, Secure Digital Card, USB Flash Disk and MicroDrive to name just a few.

Figure 5A:
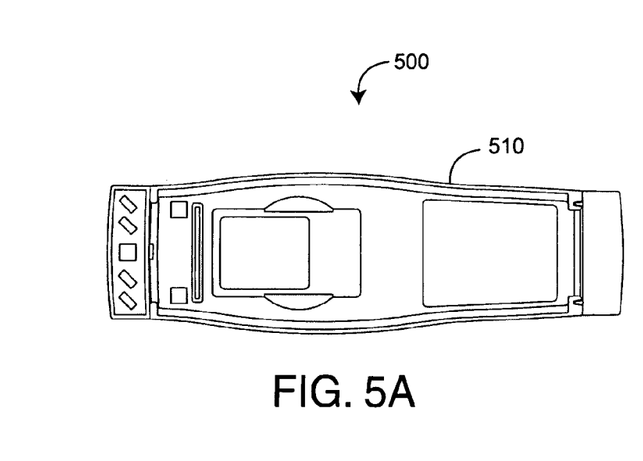
FIGS. 5A-E are front, front perspective, back, side and internal top views, respectively, of a pulse oximetry docking station incorporating a data capture system.
Figures 5B, 5D:
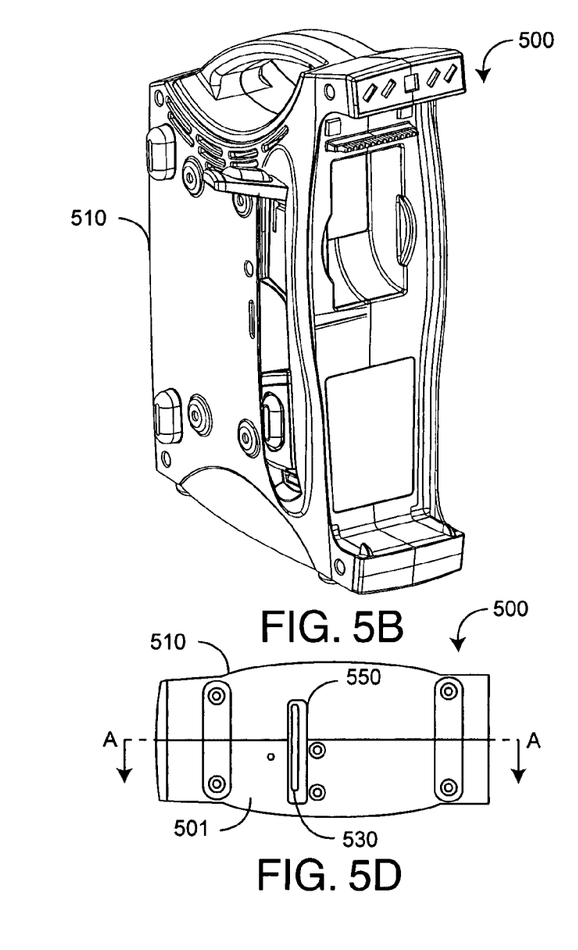
Figure 5C:
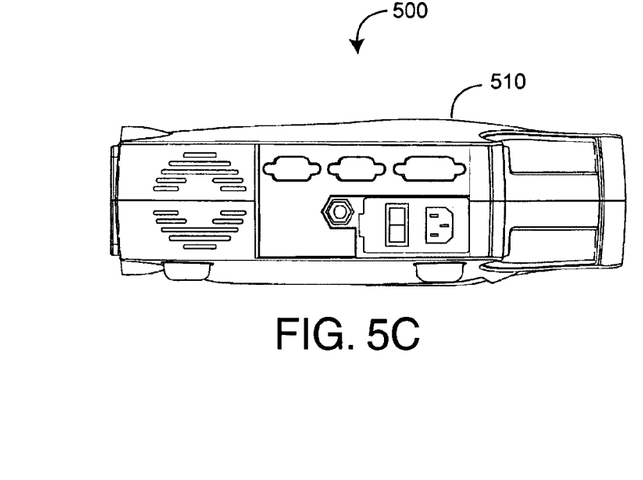
Figure 5E:
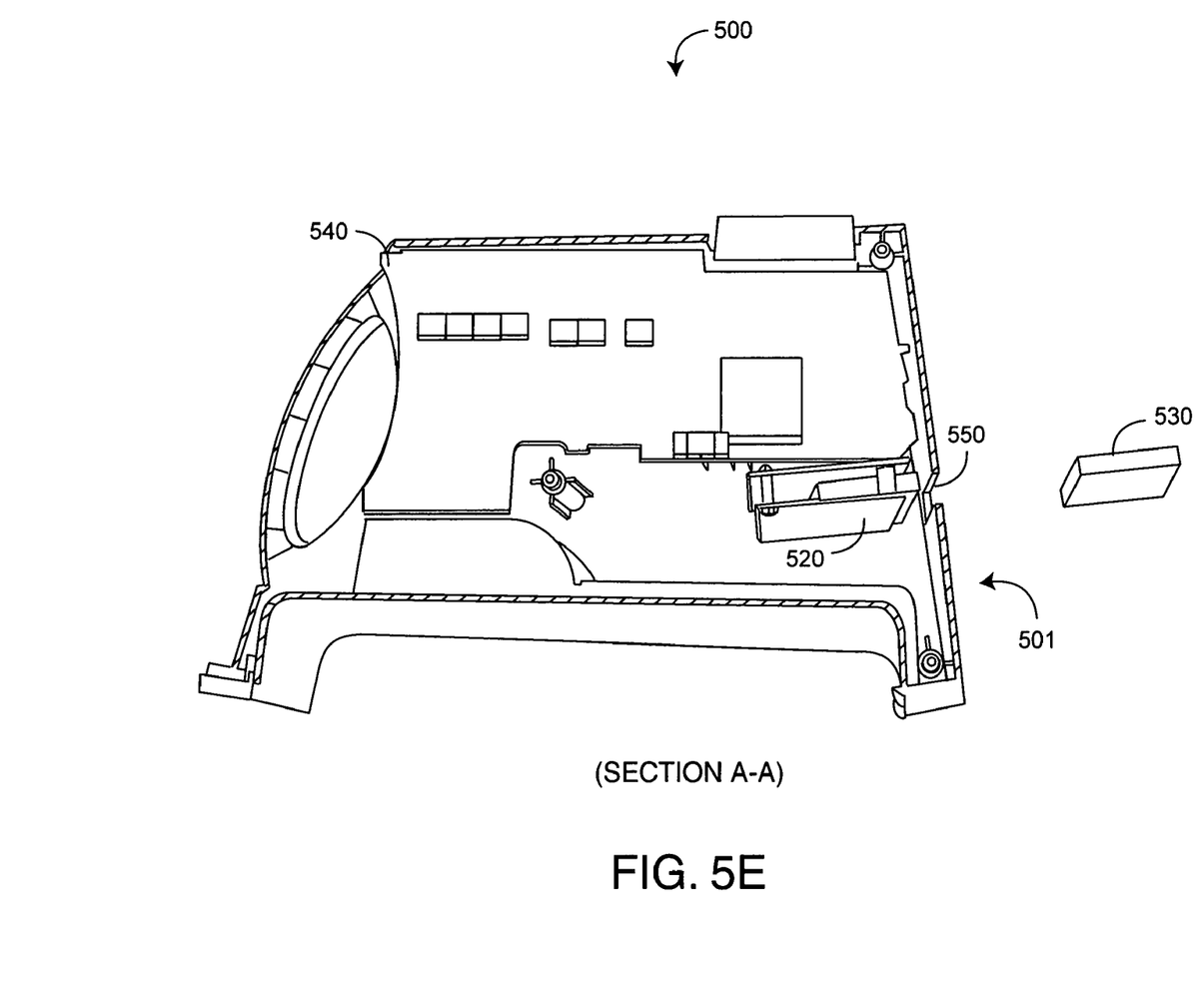
Figure 6:
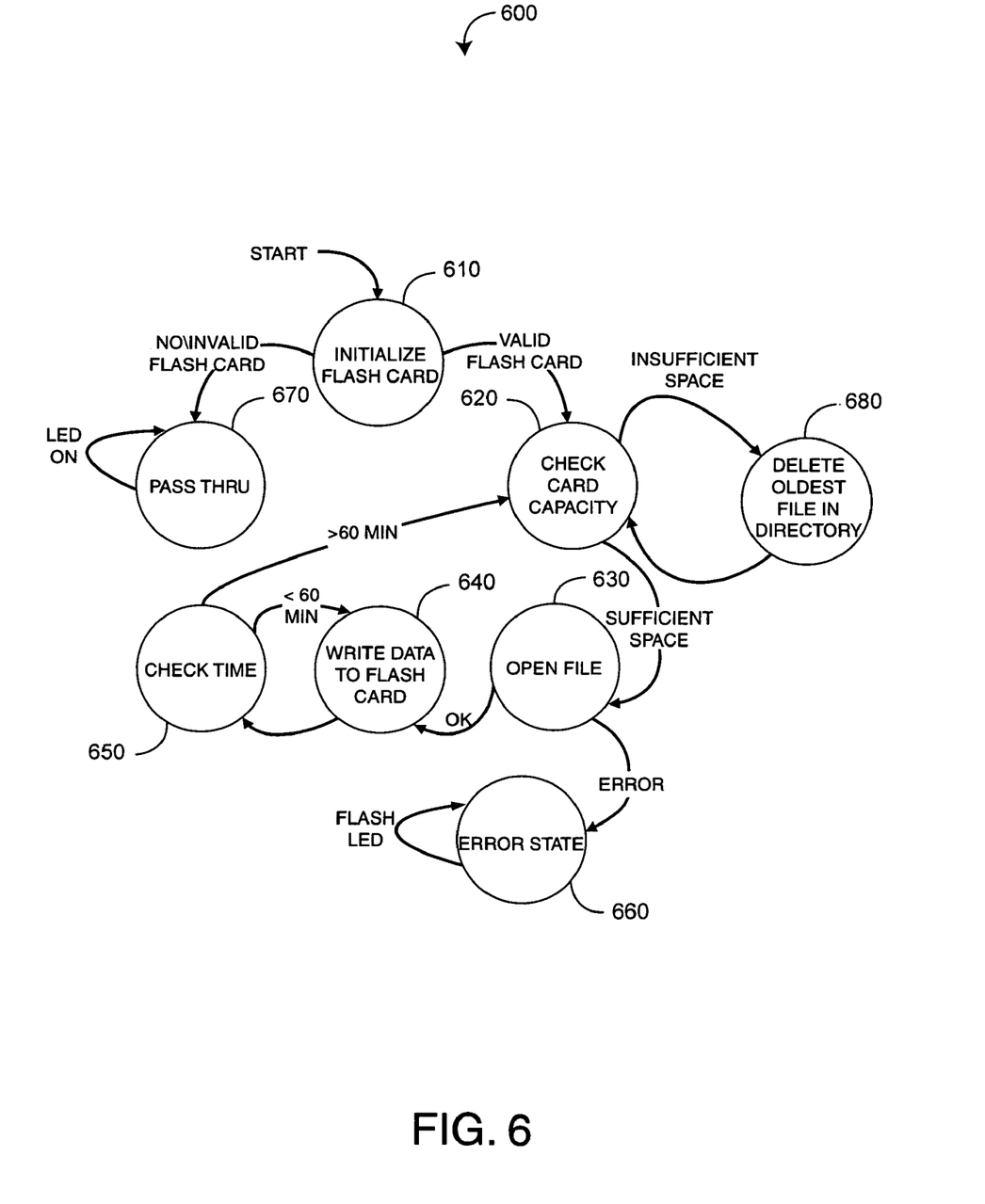
FIG. 6 is a program flow diagram for a pulse oximetry data capture system.

FIG. 6 illustrates program flow 600 for the docking station CPU to control and write data to the data storage device 520 (FIG. 5E). To start, a flash card 530 (FIG. 5E) is validated and initialized 610. If a valid flash card is in the data storage device, then the card capacity is checked 620. If the card capacity is sufficient, then a file is opened 630 and data writing begins 640. Data is advantageously written to the data storage device in multiple byte message packets at up to the IR and red signal sampling rate, as described with respect to FIG. 7, below. The writing time is checked 650. After one hour of data is recorded, the card capacity is rechecked 620 and, if sufficient, another file is opened 630 and recording continues. If an error occurs in opening a file, an LED indicator is flashed 660. If no valid flash card is detected, data is passed through to the external device signal lines and the LED indicator is turned on 670. If there is insufficient flash card capacity, the oldest file is deleted 680.

Figure 7:
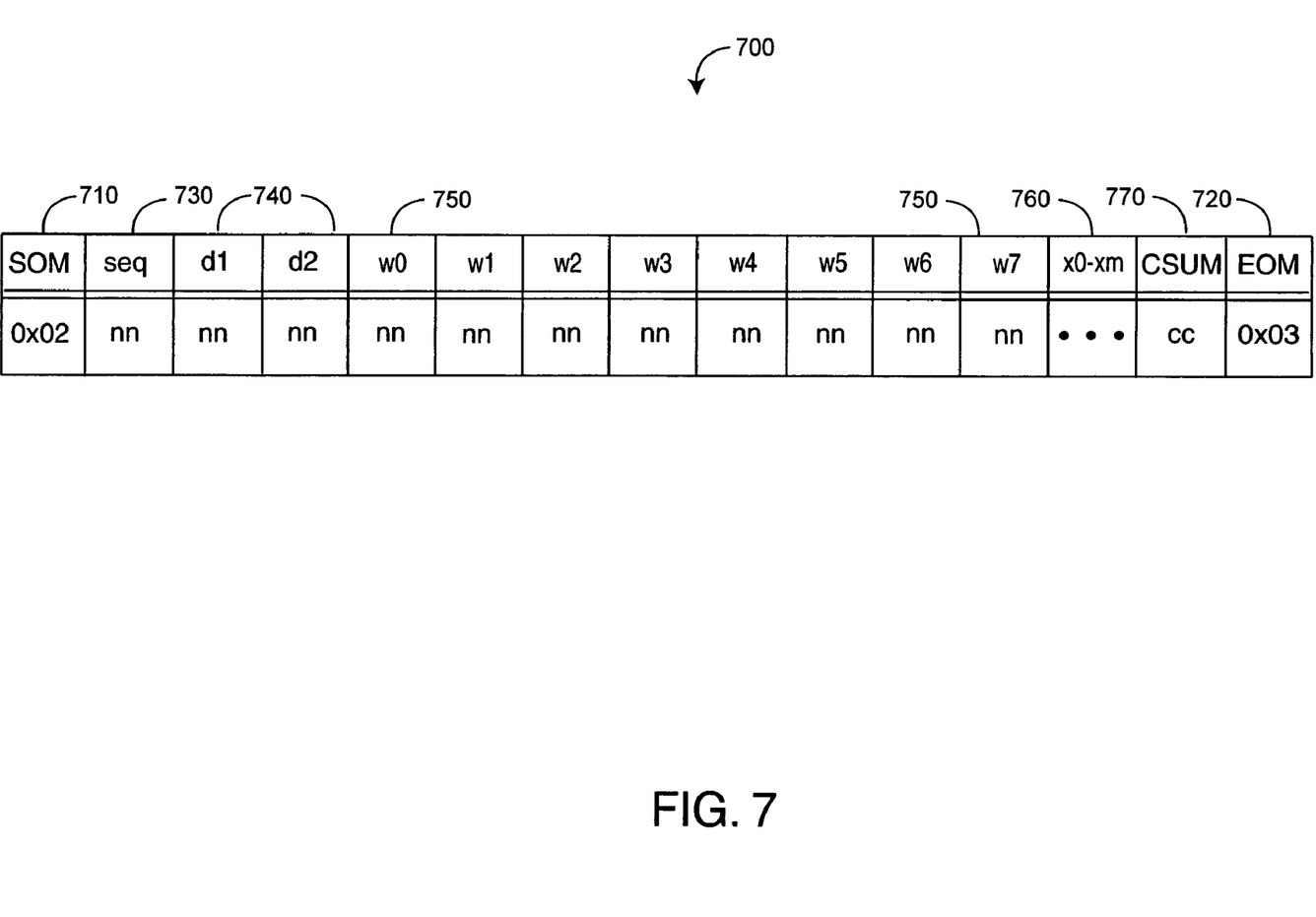
FIG. 7 is a table illustrating a multiple byte message package.

FIG. 7 illustrates a multiple byte message packet having start of message (SOM) 710, end of message (EOM) 720, sequence (seq) 730 and check sum (CSUM) 770 bytes and one or more data segments d1-d2 740, w0-w7 750 and x0-xm 760. The SOM 710 and EOM 720 are fixed-value bytes that delineate each message packet. The seq 730 byte identifies specific message packets in a cyclical group of message packets, as described below. The data segments 740-760 are formatted so as to allow storage of the data stream 322 (FIG. 3) described above. The check sum 770 is for communications error detection and is the sum of the data bytes 740-760 modulo 256. The message packets 700 are transmitted to the data storage device 420 (FIG. 4) and stored on the removable storage media 430 (FIG. 4) at about the IR and red (RD) signal sampling rate. In this manner, sufficient information with sufficient resolution is stored on the removable storage media for a thorough external data analysis.

In one embodiment, 32-bit IR waveform data can be stored in w0-w3 750, 32-bit RD waveform data can be stored in w4-w7 750, and various 16-bit output data, such as oxygen saturation and pulse rate can be stored in d1-d2 740 as identified by the sequence byte 730. In a particular embodiment, the sampling rate is 62.5 Hz, and 62 messages packets are stored in a specific sequence per second. The sequence byte (seq) 730 increments from 1 to 62 with each successive message packet 700 and then resets to 1, repeating so as to identify the specific data in, say, d1-d2 740. For example, plethysmograph waveform data is stored in w0-w7 750 at a 62 Hz rate and oxygen saturation, corresponding to seq=1 and pulse rate, corresponding to seq=2, are stored in d1-d2 740 at a sub-sampling rate of 1 Hz.

A pulse oximetry data capture system has been disclosed in detail in connection with various embodiments. These embodiments are disclosed by way of examples only and are not to limit the scope of the claims that follow. One of ordinary skill in the art will appreciate many variations and modifications.

What is claimed is:

1. A physiological monitor and data capture system capable of real-time patient monitoring and data acquisition for post-monitoring off-site analysis, the system comprising:
    a sensor having emitters configured to transmit light of at least first and second wavelengths into a fleshy medium and a detector configured to generate at least first and second intensity signals in response to receiving light after absorption by constituents of pulsatile blood flowing within the fleshy medium;
    a monitor configured to receive said intensity signals, generate digitized signals from said intensity signals at a sampling rate, compute physiological parameter data responsive to said digitized signals, and display one or more of said computed physiological parameter data responsive to said intensity signals, or trend data responsive to trends in said computed physiological data or said intensity signals; and
    a data storage device integrated with said monitor, said data storage device being configured to record on a removable storage media data at said sampling rate (sampling rate data) and data at a sub-sampling rate (sub-sampling data) using message packets having a format capable of preserving a relationship between the sampling rate data and the sub-sampling rate data, wherein said sampling rate data comprises at least a plethysmograph waveform data and said sub-sampling rate data comprises at least said computed physiological parameter or trend data.

2. The system according to claim 1 wherein said monitor comprises:
    a portable instrument that functions as a stand-alone pulse oximeter; and
    a docking station configured to receive and expand the functionality of said portable instrument, said data storage device being mounted internally to, and drawing power from, said docking station.

3. The system according to claim 2 further comprising a data path within said docking station so as to provide communications with an external device, said data storage device installed along said data path so as to capture and transparently pass-through said communications.

4. The system according to claim 3 further comprising a slot defined in a bottom wall of said docking station, said data storage device mounted inside said docking station proximate said wall, said slot providing removable storage media access to said storage device.

5. The system according to claim 1 wherein said plethysmograph waveform data comprises raw plethysmograph waveform data.

6. The system according to claim 1 wherein said sub-sampling rate data comprises oxygen saturation and pulse rate.

7. The system according to claim 6 wherein said sub-sampling rate data comprises signal quality.

8. The system according to claim 6 wherein said sub-sampling rate data comprises at least one of sensor status, monitor status, monitor settings and alarm data.

9. The system according to claim 1 wherein said sampling rate data comprises filtered plethysmograph waveform data.

10. The system according to claim 9 wherein said sub-sampling rate data comprises signal quality monitor settings and alarm data.

11. The system according to claim 1 wherein said sampling rate data comprises scaled plethysmograph data.

12. The system according to claim 11 wherein said sub-sampling rate data comprises signal quality monitor settings and alarm data.

13. The system according to claim 1, wherein said data storage device records said at least some data on the removable storage media in a cyclical group of message packets.

14. A method of capturing physiological data for post-monitoring off-site analysis, the method comprising the steps of:
    emitting light of at least first and second wavelengths;
    detecting said light after absorption by a fleshy medium site so as to generate a corresponding sensor signal;
    digitizing the sensor signal at a sampling rate;
    demodulating said digitized sensor signal so as to generate a plethysmograph;
    calculating at least oxygen saturation and pulse rate from paid plethysmograph;
    displaying one or more of said plethysmogragh, said oxygen saturation and said pulse rate, each responsive to said intensity signals; and
    writing data to a removable storage media in message packets having a format capable of preserving a relationship between data segments comprising said plethysmograph at said sampling rate along with said oxygen saturation and said pulse rate at a sub-sampling rate.

15. The data capture method according to claim 14 further comprising the steps of:
    creating a plurality of files on said removable storage media;
    recording said data in each of said files;
    checking a capacity of said removable storage media; and
    deleting an oldest one of said files if said removable storage media is over capacity.

16. The data capture method according to claim 14 further comprising the steps of:
    removing said removable storage media from a patient site after said recording step; and
    reading said removable storage media at an off-site location so as to process said data and remotely evaluate at least one of a patient, a monitor of said patient and an algorithm executing on said monitor.

17. The method of claim 14, wherein writing data to said removable storage media comprises writing data to said removable storage media in a cyclical group of message packets.

18. A physiological data capture system configured to acquire data for post-monitoring off-site analysis, the system comprising:
    a sensor adapted to generate an intensity signal responsive to light absorption by constituents of pulsatile blood flowing within a fleshy medium;
    a digitizer receiving said intensity signal and generating a digital plethysmograph signal at a sampling rate;
    a signal processor receiving said plethysmograph signal, calculating an oxygen saturation and pulse rate, and outputting for display one or more of said plethysmograph signal, calculated oxygen saturation, or pulse rate, each responsive to said intensity signals;
    a data storage device configured to write said plethysmograph signal, oxygen saturation and pulse rate into message packets having a format capable of preserving a relationship between the plethysmograph signal at the sampling rate with the oxygen saturation and pulse rate data at a sub-sampling rate;

a storage media configured to be removably loaded into said data storage device or removed to an off-site location for post-monitoring off-site analysis of the plethysmograph signal, calculated oxygen saturation, and pulse rate data based on data written into the message packets, said data storage device writing said plethymograph to said storage media at said sampling rate, along with said oxygen saturation and said pulse rate at a sub-sampling rate.

19. The data capture system according to claim 18 further comprising:
- a data port adapted to communicate with an external device; and
- a communications path between said signal processor and said data port configured to output said plethysmograph, oxygen saturation and pulse rate to said external device;

wherein said data storage device is installed along said communications path and configured to transparently capture and write said plethysmograph to said removable storage media.

20. The data capture system according to claim 19 further comprising:
- a portable instrument having said digitizer;
- a docking station configured to accept said portable instrument and housing said data storage device; and
- a plurality of UART signals provided between said docking station and said data storage device along said communications path.

21. The data capture system of claim 18, wherein said data storage device writes said plethysmograph signal, oxygen saturation and pulse rate into a cyclical group of message packets.

* * * * *